United States Patent [19]

Narayan et al.

[11] Patent Number: 5,618,967
[45] Date of Patent: Apr. 8, 1997

[54] ISOCYANATE COMPOSITION

[75] Inventors: Thirumurti Narayan, Grosse Ile; Valeri L. Voloppi, Riverview, both of Mich.

[73] Assignee: BASF Corporation, Mt. Olive, N.J.

[21] Appl. No.: 551,193

[22] Filed: Oct. 30, 1995

[51] Int. Cl.$^6$ .............................. C07C 261/00; C08J 9/34
[52] U.S. Cl. .............................. 560/26; 521/51; 521/159; 521/174; 521/914; 528/77; 560/359
[58] Field of Search .............................. 521/51, 159, 174, 521/914; 560/26, 359; 528/77

[56] References Cited

U.S. PATENT DOCUMENTS

| | | | |
|---|---|---|---|
| 4,289,856 | 9/1981 | Yamamoto et al. | 521/51 |
| 4,792,576 | 12/1988 | Nodelman | 521/174 |
| 4,994,502 | 2/1991 | Markovs et al. | 54/137 |
| 5,059,633 | 10/1991 | Lutter et al. | 546/160 |
| 5,164,423 | 11/1992 | DeGenova et al. | 521/159 |
| 5,166,183 | 11/1992 | Franyutti et al. | 521/51 |
| 5,189,068 | 2/1993 | Boehme et al. | 521/51 |
| 5,216,035 | 6/1993 | Harrison et al. | 521/51 |
| 5,234,961 | 8/1993 | Tanis | 521/51 |
| 5,236,960 | 8/1993 | Harrison et al. | 521/51 |
| 5,236,961 | 8/1993 | Ho et al. | 521/116 |
| 5,284,880 | 2/1994 | Harrison et al. | 521/51 |
| 5,338,820 | 8/1994 | Harrison et al. | 528/67 |
| 5,369,138 | 11/1994 | Gansen et al. | 521/159 |
| 5,389,693 | 2/1995 | DeGenova et al. | 521/51 |

FOREIGN PATENT DOCUMENTS

| | | |
|---|---|---|
| 0257441A2 | 3/1988 | European Pat. Off. . |
| WO91/17197 | 11/1991 | WIPO . |

Primary Examiner—Morton Foelak
Attorney, Agent, or Firm—Mary E. Golota

[57] ABSTRACT

The present invention to water-blown integral skin polyurethane foam compositions, molded polyurethane articles, a process of preparing said articles, and an isocyanate composition for use therein. In particular, the invention relates to water-blown integral skin molded polyurethane articles having particularly advantageous physical properties, and compositions useful for producing such articles.

In particular, the invention provides a polyurethane composition which has an isocyanate component (a) an isocyanate reactive component (b), a blowing agent comprising water (c), a polyether (d) selected from the group consisting of polytetrahydrofuran and polyethylene glycol having a number average molecular weight of from 200 to 2000 and optionally, one or more additives (e) from the group consisting of catalysts, chain extenders, oxo alcohols, and mixtures thereof. The composition may be characterized in that the integral skin polyurethane articles made of the composition have a tensile strength of greater than or equal to 450 psi and/or a Taber abrasion (mg loss) of less than 200.

5 Claims, No Drawings

ISOCYANATE COMPOSITION

FIELD OF THE INVENTION

The present invention relates to water-blown integral skin polyurethane foam compositions, molded polyurethane articles, a process of preparing said articles, and an isocyanate composition for use therein. In particular, the invention relates to water-blown integral skin molded polyurethane articles having particularly advantageous physical properties, and compositions useful for producing such articles.

BACKGROUND OF THE INVENTION

Integral skin polyurethane foams are well known to those skilled in the art. Such foams typically have a cellular interior and a high density microcellular or noncellular skin. In general, integral skin foams are prepared from the reaction of an organic isocyanate with a substance having at least one isocyanate reactive group in the presence of one or more catalysts, blowing agents, and a variety of optional additives. The reaction is typically carried out in a mold where a higher density skin forms at the interface of the reaction mixture and the relatively cool interior surface of the mold.

Traditionally, integral skin polyurethane foams were expanded with the use of chlorofluorocarbons (CFCs) blowing agent or hydrogenated chlorofluorocarbons (HCFCs) blowing agents. However, because of environmental concerns, government regulations now mandate the reduction and eventual elimination of CFCs and HCFCs in integral skin foam production.

As a result, the polyurethane industry has devoted considerable time and energy in developing alternative blowing agents which produce integral skin foams having performance and processing properties that are at least equivalent to, or better than, those of traditional CFC and HCFC blowing agents.

It has been particularly difficult to find alternative blowing agents suitable for use in integral skin foams intended for use in shoe soles. Such foams must have a cosmetically acceptable appearance and a smooth surface with a good feel. In addition, they must exhibit enhanced resistance to abrasion and cracking on flex. Such particular properties must be in addition to optimum values of tensile strength, tear strength, and elongation.

One alternative blowing agent that has found particular favor with the makers of integral skin foams intended for use in shoe soles is 1,1,1,2-tetrafluoroethane or HFC-134a. Foams produced with HFC-134a alone or in combination with other blowing agents, such as water, exhibit generally adequate physical properties.

However, the use of HFC-134a has several problems. HFC-134a is a gas and is not readily soluble in typical polyurethane resin systems. As a result, special equipment is needed for addition. Processing problems become more acute as ambient temperatures increase. Also, environmental concerns about the global warming potential of HFC-134a have been raised.

Accordingly, manufacturers of integral skin polyurethane shoe soles are increasingly requesting alternatives to HFC-134a-blown polyurethane compositions. In particular, there is a great desire for a solely water blown polyurethane system capable of producing integral skin foams exhibiting performance properties suitable for use as shoe soles.

There have been several attempts to produce such solely water blown integral skin polyurethane compositions.

For example, WO 91/17197 discloses microcellular polyurethane polymers prepared from isocyanate-terminated poly(oxytetramethylene) glycol prepolymers. The Isocyanate compound is a isocyanate-terminated prepolymer, having an isocyanate content of from 14 to 28 percent, which is obtained by reacting an isocyanate containing at least 70 weight percent 4,4'-methylene diphenyl isocyanate with a poly(oxytetramethylene) glycol which has an average hydroxyl equivalent weight of from 250 to 1500.

However, the WO 91/17197 specification teaches that the blowing agent need not comprise solely water and may contain halogenated hydrocarbons and preferably chlorofluorocarbons such as trichlorodifluoroethane and/or trichlorofluoroethane.

It is thus an object of the invention to provide a solely water blown integral skin polyurethane composition suitable for making shoe soles.

In particular, it is an object of the invention to provide an integral skin polyurethane composition capable of making integral skin polyurethane articles characterized by a tensile strength of greater than or equal to 450 psi and/or a Taber Abrasion (mg loss) of less than 200.

It is another object of the invention to provide integral skin polyurethane molded articles, suitable for making shoe soles, characterized by a tensile strength of greater than or equal to 450 psi and/or a Taber Abrasion (mg loss) of less than 200.

It is a further object of the invention to provide a process of making such integral skin polyurethane molded articles.

Finally, it is an object of the invention to provide an isocyanate composition for use in polyurethane compositions intended for use in the production of integral skin polyurethane articles suitable for use in shoe soles.

An advantage of the present invention is that a blowing agent consisting of water can be used in the production of integral skin polyurethane articles exhibiting performance properties which are at least equivalent to or better than those achieved with traditional blowing agents.

SUMMARY OF THE INVENTION

The present invention achieves one or more of the foregoing objects and advantages by providing a polyurethane composition which has an isocyanate component (a), an isocyanate reactive component (b), a blowing agent comprising water (c), a polyether (d) selected from the group consisting of polytetrahydrofuran and polyethylene glycol having a number average molecular weight of from 200 to 2000, and optionally, one or more additives (e) selected from the group consisting of catalysts, chain extenders, oxo alcohols, and mixtures thereof. The composition may be characterized in that integral skin polyurethane articles made of the composition have a tensile strength of greater than or equal to 450 psi and/or a Taber Abrasion (mg loss) of less than 200.

The polyurethane composition of the invention further comprises isocyanate component (a) which comprises the reaction product of (a1) a polyoxypropylated propylene glycol having an OH number of from 200 to 300, (a2) a diol selected from the group consisting of dipropylene glycol and tripropylene glycol, (a3) a polyoxypropylated/ethoxylated glycerine having an OH number of from 20 to 50, (a4) a polyoxypropylated/ethoxylated glycol having an OH number of from 15 to 45, and (a5) diphenylmethane diisocyanate.

The polyurethane composition of the invention may also be characterized in that the isocyanate reactive component (b) comprises (b1) a propoxylated and ethoxylated diol initiated polyol having an OH number of from 10 to 40, (b2) a graft polyol having from 5 to 55 percent by weight of a polymerized monomer selected from the group consisting of styrene, acrylonitrile, and mixtures thereof, and a carrier polyol having an OH number of from 20 to 50, and (b3) a propoxylated and ethoxylated triol initiated polyol having an OH of from 15 to 45.

Another object of the invention is achieved with a novel process for making integral skin polyurethane articles, wherein the process requires the providing of an isocyanate component (a) such as that described above, providing a resin side (I) comprising an isocyanate reactive component (b) such as that described above, the blowing agent (c) comprising water, a polyether (d) selected from the group consisting of polytetrahydrofuran and polyethylene glycol having a number average molecular weight or from 200 to 2000, and optionally, one or more additives (e) selected from the group consisting of catalysts, chain extenders, oxo alcohols and mixtures thereof. The process further involves the introduction of the isocyanate component (a) and resin side (I) into a mold and reacting component (a) and resin side (I) together for a time sufficient to produce integral skin polyurethane articles. The process may be characterized inasmuch as integral skin polyurethane articles made by the process have a tensile strength of greater than or equal to 450 psi and/or a Taber Abrasion (mg loss) of less than 200.

Yet another of the foregoing objects is achieved with the provision of integral skin polyurethane molded articles which are achieved from the foregoing process.

Finally, an object of the invention is achieved with the provision of an isocyanate composition (a) which comprises the reaction product of (a1) a polyoxypropylated propylene glycol having an OH number of from 200 to 300, (a2) a diol selected from the group consisting of dipropylene glycol and tripropylene glycol, (a3) a polyoxypropylated/ethoxylated glycerine having an OH number of from 20 to 50, (a4) a polyoxypropylated/ethoxylated glycol having an OH number of from 15 to 45, and (a5) diphenylmethane diisocyanate. The isocyanate composition of the invention has a percent NCO of from 16 to 20, and further comprises a blend of the reaction product of (a1) a polyoxypropylated propylene glycol having an OH number of from 200 to 300, (a2) dipropylene glycol and tripropylene glycol, and (a5) diphenylmethane diisocyanate, the reaction product of (a3) a polyoxypropylated/ethoxylated glycerine having an OH number of from 20 to 50 and (a5) diphenylmethane diisocyanate, and the reaction product of (a4) a polyoxypropylated/ethoxylated glycol having an OH number of from 15 to 45, and (a5) diphenylmethane diisocyanate.

DETAILED DESCRIPTION OF THE INVENTION

The polyurethane composition of the invention requires the use of an isocyanate component (a), an isocyanate reactive component (b), a blowing agent (c) comprising water, a polyether (d) selected from the group consisting of polytetrahydrofuran and polyethylene glycol having a number average molecular weight of from 200 to 2000, and optionally, one or more additives (e) selected from the group consisting of catalysts, chain extenders, oxo alcohols and mixtures thereof. It should be appreciated that for purposes of the instant invention, components (b), (c), (d), and (e) may be combined and termed the resin side, or resin side (I).

The isocyanate component (a) can typically contain aromatically bound isocyanate groups. Representative of the types of organic polyisocyanates contemplated for use herein include, for example, 1,4-diisocyanatobenzene, 1,3-diisocyanato-o-xylene, 1,3-diisocyanato-p-xylene, 1,3-diisocyanato-m-xylene, 2,4-diisocyanato-1-chlorobenzene, 2,4-diisocyanato-1-nitrobenzene, 2,5-diisocyanato-1-nitrobenzene, m-phenylene diisocyanate, 2,4-toluene diisocyanate, 2,6-toluene diisocyanate, mixtures of 2,4- and 2,6-toluene diisocyanate, hexahydrotoluene diisocyanate, 1,5-naphthalene diisocyanate, 1-methoxy-2,4-phenylene diisocyanate, 2,4'diphenylmethane diisocyanate, 4,4'-diphenylmethane diisocyanate, 4,4'-biphenylene diisocyanate, 3,3'-dimethyl-4,4'-diphenylmethane diisocyanate, the triisocyanates such as 4,4',4"-triphenylmethane triisocyanate, polymethylene polyphenylene polyisocyanate, and 2,4,6-toluene triisocyanate; and the tetraisocyanates such as 4,4-dimethyl-2,2'-5,5'-diphenylmethane tetraisocyanate. Especially useful due to their availability and properties are 2,4'-diphenylmethane diisocyanate, 4,4'-diphenylmethane diisocyanate, and mixtures thereof.

These polyisocyanates are prepared by conventional methods known in the art such as the phosgenation of the corresponding organic amine. Included within the usable isocyanates are the modifications of the above isocyanates which contain carbodiimide, allophanate, or isocyanurate structures.

Prepolymers may also be, and preferably will be, employed in the process of the subject invention. These prepolymers are prepared by reacting an excess of organic polyisocyanate or mixtures thereof with a minor amount of an active hydrogen-containing compound determined by the well-known Zerewitinoff Test, as described by Kohler in *Journal of the American Chemical Society*, 49, 3181 (1927). Generally, the prepolymers have a free isocyanate content of from 15 percent to 30 percent by weight.

However, while the foregoing generally describes the isocyanate component (a), it is most preferred that isocyanate component (a) be comprised of an isocyanate prepolymer having a percent free NCO of from 16 to 20, and most preferably, from 17 to 19.

The reactive hydrogen-containing compound used in the preparation of isocyanate component (a) may be one or more polyoxyalkylene polyether polyols such as those described below with respect to isocyanate reactive component (b). Preferred polyoxyalkylene polyether polyols are those resulting from the polymerization of a polyhydric alcohol and an alkylene oxide. Mixtures of such polyoxyalkylene polyether polyols are particularly preferred. The most preferred mixtures are those having polyols of a variety of number average molecular weights and functionalities.

Such blends of polyoxyalkylene polyether polyols may be reacted with one or more of the foregoing aromatically bound polyisocyanates. However, it is particularly preferred that a mixture of polyoxyalkylene polyether polyols be reacted with an (a5) isocyanate which comprises diphenylmethane diisocyanate. Most preferably, it has been found that the various polyether polyols be reacted with an isocyanate (a5) that is predominantly 4,4'-diphenylmethane diisocyanate. Ideally, the final product (a) will contain less than 5 percent 2,4'-diphenylmethane diisocyanate. Most preferably, the final product (a) will contain less than 3 percent 2,4'-diphenylmethane diisocyanate.

A particularly suitable blend of polyoxyalkylene polyether alcohols has been found to be comprised of (a1) a polyoxypropylated propylene glycol, (a2) a diol selected from the group consisting of dipropylene glycol and tripropylene glycol, (a3) a polyoxypropylated/ethoxylated glycerine, and (a4) a polyoxypropylated/ethoxylated glycol. Such particular blend of polyoxyalkylene polyether polyols has been found to produce a particularly suitable reaction product when reacted with an excess amount of (a5) diphenylmethane diisocyanate and ideally, 4,4'MDI.

The polyoxypropylated propylene glycol (a1) may have a number average molecular weight of from 200 to 600, preferably from 300 to 500, and most preferably from 350 to 450. In addition, the polyoxypropylated propylene glycol (a1) will also have a hydroxyl number of from 200 to 300, preferably from 240 to 280, and most preferably from 250 to 270.

Polyol (a2) will be a diol selected from the group consisting of dipropylene glycol and tripropylene glycol. Dipropylene glycol is most preferred.

Polyoxypropylated/ethoxylated glycerine (a3) may have a number average molecular weight of from 1000 to 7000, and preferably from 2000 to 5000, and most preferably from 3000 to 5000. The polyol (a3) may also have a hydroxyl number of from 20 to 50, but will preferably have a hydroxyl number of from 25 to 45, and most preferably from 30 to 40. The percentage of residual alkylene oxide groups attributable to propylene oxide should be from 65 to 95 percent, and preferably from 75 to 85 percent, with the remainder being residual ethylene oxide groups.

Polyoxypropylated/ethoxylated glycol (a4) may have a number average molecular weight of from 500 to 7000, and preferably from 2000 to 5000. Most preferably, the polyol (a4) will have a number average molecular weight of between 3000 to 4000. The percentage of residual alkylene oxide groups attributable to propylene oxide will preferably be from between 65 to 95 percent, and most preferably between 75 to 85 percent, with the remainder of residual alkylene oxide groups being those of ethylene oxide. Polyol (a4) will generally have an OH number of from 15 to 45, preferably from 20 to 40, and most preferably from 25 to 35.

It will be appreciated by those skilled in the art that isocyanate component (a) may comprise the reaction product of (a1), (a2), (a3), (a4), and (a5) as well as a blend of reaction products arising from various combinations of (a1), (a2), (a3), (a4) and (a5). An example of one method of preparing the isocyanate component (a) of the invention involves the simultaneous reaction of components (a1), (a2), (a3), (a4) and (a5). The diphenylmethane diisocyanate, along with a suitable reaction initiator, is charged to a preheated reactor wherein the contents are heated to a temperature of between 50° to 120° C. Subsequently, a polyoxyalkylene polyether polyol blend comprising (a1), (a2), (a3) and (a4) is added and reacted for a time of between one to seven hours. Reaction times of from 1 to 4 hours are most preferred.

Alternatively, however, isocyanate component (a) may be prepared as a blend of (1) the reaction product of polyoxypropylated propylene glycol (a1), a diol selected from the group consisting of dipropylene glycol and tripropylene glycol (a2), and diphenylmethane diisocyanate (a5); (2) the reaction product of polyoxypropylated/ethoxylated glycerine (a3), and diphenylmethane diisocyanate (a5); and (3) the reaction product of polyoxypropylated/ethoxylated glycol (a4) and diphenylmethane diisocyanate (a5). Such a method is most preferred.

Regardless of the method used to make the isocyanate component (a) of the invention, it has been found that the isocyanate composition (a) of the invention may be characterized as generally comprising from 2 to 70 percent by weight diphenylmethane diisocyanate, preferably from 30 to 55 percent by weight, and most preferably from 40 to 50 percent diphenylmethane diisocyanate. Most preferably, the diphenylmethane diisocyanate (a5) will be comprised almost exclusively of 4,4'-diphenylmethane diisocyanate, with only residual amounts of 2,4'-diphenylmethane diisocyanate present. In particular, as indicated above, such percentages of 2,4'-diphenylmethane diisocyanate should be less than 5 percent, and preferably less than 3 percent of the overall isocyanate composition (a).

In addition, isocyanate component (a) should also contain from 1 to 30 percent by weight, based on the total weight of the isocyanate component (a), of an isocyanate-terminated prepolymer (I) which is a reaction product of (a1) polyoxypropylated propylene glycol with (a5) diphenylmethane diisocyanate. Preferably, this isocyanate terminated prepolymer will be present in an amount of 1 to 20 percent, and most preferably from 1 to 10 percent by weight, based on the total weight of isocyanate component (a).

In addition, isocyanate component (a) should further contain from 5 to 40 percent by weight of an isocyanate terminated prepolymer (II) which is the reaction product of a diol selected from the group consisting of dipropylene glycol and tripropylene glycol (a2) and diphenylmethane diisocyanate (a5). Preferably, such prepolymer species should be present in an amount of between 10 to 30 percent, and most preferably from 15 to 25 percent by weight of the total amount of isocyanate component (a).

Additionally, isocyanate component (a) should further contain from 1 to 30 percent by weight of an isocyanate terminated prepolymer (III) which is the reaction product of polyoxypropylated/ethoxylated glycol (a4) and diphenylmethane diisocyanate (a5). More preferably, such isocyanate terminated prepolymer species will be present in an amount of from 5 to 25 percent, and most preferably from 10 to 20 percent.

Finally, isocyanate component (a) should further contain from 1 to 30 percent by weight of an isocyanate terminated prepolymer (IV) which is the reaction product of polyoxypropylated/ethoxylated glycerine (a3) and diphenylmethane diisocyanate (a5). More preferably, such isocyanate terminated prepolymer will be present in an amount between 5 and 25 percent by weight, and most preferably, from 10 to 20 percent by weight of the overall isocyanate component (a).

The polyurethane composition of the invention further requires isocyanate reactive component (b). Preferably, polyhydroxyl compounds having a functionality of 1.7 to 8, more preferably 1.7 to 4, and an average hydroxyl number of 15 to 850, more preferably 20 to 400, are examples of suitable polyols for use in isocyanate reactive component (b). Polyols having hydroxyl numbers outside this range may be used, but it is preferred that the average hydroxyl number for the total amount of polyols used fall within the range of 20 to 100.

Examples include polythioether polyols, polyester amides and polyacetals containing hydroxyl groups, aliphatic polycarbonates containing hydroxyl groups, amine terminated polyoxyalkylene polyethers, polyester polyols, and preferably polyoxyalkylene polyether polyols, and graft dispersion polyols. In addition, mixtures of at least two of the aforesaid polyols can be used as long as the combination has an average hydroxyl number in the aforesaid range.

Polyoxyalkylene polyether polyols, which can be obtained by known methods, are preferred for use as the polyhydroxyl compounds. For example, polyether polyols can be produced by anionic polymerization with alkali hydroxides such as sodium hydroxide or potassium hydroxide or alkali alcoholates, such as sodium methylate, sodium ethylate, or potassium ethylate or potassium isopropylate as catalysts and with the addition of at least one initiator molecule containing 1.7 to 8, preferably 1.7 to 4, reactive hydrogens or by cationic polymerization with Lewis acids such as antimony pentachloride, boron trifluoride etherate, etc., or bleaching earth as catalysts from one or more alkylene oxides with 2 to 4 carbons in the alkylene radical. Any suitable alkylene oxide may be used such as 1,3-propylene oxide, 1,2- and 2,3-butylene oxide, amylene oxides, styrene oxide, and preferably ethylene oxide and 1,2-propylene oxide and mixtures of these oxides. The polyalkylene polyether polyols may be prepared from other starting materials such as tetrahydrofuran and alkylene oxide-tetrahydrofuran mixtures; epihalohydrins such as epichlorohydrin; as well as aralkylene oxides such as styrene oxide. The polyalkylene polyether polyols may have either primary or secondary hydroxyl groups.

Included among the polyether polyols are polyoxyethylene glycol, polyoxypropylene glycol, polyoxybutylene glycol, polytetramethylene glycol, block copolymers, for example, combinations of polyoxypropylene and polyoxyethylene glycols, poly-1,2-oxybutylene and polyoxyethylene glycols, poly-1,4-tetramethylene and polyoxyethylene glycols, and copolymer glycols prepared from blends of sequential addition of two or more alkylene oxides. The polyalkylene polyether polyols may be prepared by any known process such as, for example, the process disclosed by Wurtz in 1859 and *Encyclopedia of Chemical Technology*, Vol. 7, pp. 257–262, published by Interscience Publishers, Inc. (1951) or in U.S. Pat. No. 1,922,459.

Polyethers which are preferred include the alkylene oxide addition products of polyhydric alcohols such as ethylene glycol, propylene glycol, dipropylene glycol, trimethylene glycol, 1,2-butanediol, 1,3-butanediol, 1,4-butanediol, 1,2-pentanediol, 1,4-pentanediol, 1,5-pentanediol, 1,6-hexanediol, 1,7-heptanediol, hydroquinone, resorcinol, glycerol, glycerine, 1,1,1-trimethylolpropane, 1,1,1-trimethylolethane, pentaerythritol, 1,2,6-hexanetriol, α-methyl glucoside, sucrose, and sorbitol. Also included within the term "polyhydric alcohol" are compounds derived from phenol such as 2,2-bis(4-hydroxyphenyl)-propane, commonly known as Bisphenol A.

Suitable organic amine starting materials include aliphatic and cycloaliphatic amines and mixtures thereof, having at least one primary amino group, preferably two or more primary amino groups, and most preferable are the diamines. Specific non-limiting examples of aliphatic amines include monoamines having 1 to 12, preferably 1 to 6, carbon atoms, such as methylamine, ethylamine, butylamine, hexylamine, octylamine, decylamine and dodecylamine; aliphatic diamines such as 1,2-diaminoethane, propylene diamine, 1,4-diaminobutane, 1,6-diaminohexane, 2,2-dimethyl-1,3-propanediamine, 2-methyl-1,5-pentadiamine, 2,5-dimethyl-2,5-hexanediamine, and 4-aminomethyloctane-1,8-diamine, and amino acid-based polyamines such as lysine methyl ester, lysine aminoethyl ester and cystine dimethyl ester; cycloaliphatic monoamines of 5 to 12, preferably of 5 to 8, carbon atoms in the cycloalkyl radical, such as cyclohexylamine and cyclo-octylamine and preferably cycloaliphatic diamines of 6 to 13 carbon atoms, such as cyclohexylenediamine, 4,4'-, 2,4'-, and 2,2'-diaminocyclohexylmethane and mixtures thereof; aromatic monoamines of 6 to 18 carbon atoms, such as aniline, benzylamine, toluidine and naphthylamine and preferably aromatic diamines of 6 to 15 carbon atoms, such as phenylenediamine, naphthylenediamine, fluorenediamine, diphenyldiamine, anthracenediamine, and preferably 2,4- and 2,6-toluenediamine and 4,4'-, 2,4'-, and 2,2'-diaminophenylmethane, and aromatic polyamines such as 2,4,6-triaminotoluene, mixtures of polyphenyl-polymethylene-polyamines, and mixtures of diaminidiphenylmethanes and polyphenyl-polymethylene-polyamines. Preferred are ethylenediamine, propylenediamine, decanediamine, 4,4'-diaminophenylmethane, 4,4'-diaminocyclohexylmethane, and toluenediamine.

Suitable initiator molecules also include alkanolamines such as ethanolamine, diethanolamine, N-methyl- and N-ethylethanolamine, N-methyl- and N-ethyldiethanolamine and triethanolamine plus ammonia.

Suitable polyhydric polythioethers which may be condensed with alkylene oxides include the condensation product of thiodiglycol or the reaction product of a dicarboxylic acid.

Polyhydroxyl-containing phosphorus compounds which may be used include those compounds disclosed in U.S. Pat. No. 3,639,542. Preferred polyhydroxyl-containing phosphorus compounds are prepared from alkylene oxides and acids of phosphorus having a $P_2O_5$ equivalency of from about 72 percent to about 95 percent.

Suitable polyacetals which may be condensed with alkylene oxides include the reaction product of formaldehyde or other suitable aldehyde with a dihydric alcohol or an alkylene oxide such as those disclosed above.

Suitable aliphatic thiols which may be condensed with alkylene oxides include alkanethiols containing at least two -SH groups such as 1,2-ethanedithiol, 1,2-propanedithiol, 1,6-hexanedithiol; alkene thiols such as 2-butene-1,4-dithiol; and alkyne thiols such as 3-hexyne-1,6-dithiol.

Also preferred as the polyol are polymer modified polyols, in particular, the so-called graft polyols. Graft polyols are well known to the art and are prepared by the in situ polymerization of one or more vinyl monomers, preferably acrylonitrile and styrene, in the presence of a polyether or polyester polyol, particularly polyols containing a minor amount of natural or induced unsaturation. Methods of preparing such graft polyols may be found in columns 1–5 and in the Examples of U.S. Pat. No. 3,652,639; in columns 1–6 and the Examples of U.S. Pat. No. 3,823,201; particularly in columns 2–8 and the Examples of U.S. Pat. No. 4,690,956; and in U.S. Pat. No. 4,524,157; all of which patents are herein incorporated by reference.

Non-graft polymer modified polyols are also preferred, by example, those prepared by the reaction of a polyisocyanate with an alkanolamine in the presence of a polyol as taught by U.S. Pat. Nos. 4,293,470; 4,296,213; and 4,374,209; dispersions of polyisocyanurates containing pendant urea groups as taught by U.S. Pat. No. 4,386,167; and polyisocyanurate dispersions also containing biuret linkages as taught by U.S. Pat. No. 4,359,541. Other polymer modified polyols may be prepared by the in situ size reduction of polymers until the particle size is less than 20 μm, preferably less than 10 μm.

Illustrative polymerization initiators which may be employed are the well-known free radical types of vinyl polymerization initiators such as the peroxides, persulfates, perborates, percarbonates, azo compounds, etc. These include hydrogen peroxide, dibenzoyl peroxide, acetyl peroxide, benzoyl hydroperoxide, t-butyl hydroperoxide, di-t- butyl peroxide, lauroyl peroxide, butyryl peroxide, diisopropylbenzene hydroperoxide, cumene hydroperoxide, paramenthane hydroperoxide, diacetyl peroxide, di$\alpha$-cumyl peroxide, dipropyl peroxide, diisopropyl peroxide, isopropyl-t-butyl peroxide, butyl-t-butyl peroxide, difuroyl peroxide, bis(triphenylmethyl) peroxide, bis(p-methoxybenzoyl) peroxide, p-monomethoxybenzoyl peroxide, rubene peroxide, ascaridol, t-butyl peroxybenzoate, diethyl peroxyterephthalate, propyl hydroperoxide, isopropyl hydroperoxide, n-butyl hydroperoxide, t-butyl hydroperoxide, cyclohexyl hydroperoxide, trans-decalin hydroperoxide, $\alpha$-methylbenzyl hydroperoxide, $\alpha$-methyl-$\alpha$-ethyl benzyl hydroperoxide, tetralin hydroperoxide, triphenylmethyl hydroperoxide, diphenylmethyl hydroperoxide, $\alpha,\alpha'$-azobis-(2-methyl heptonitrile), 1-t-butylazo-1-cyanocyclohexane, persuccinic acid, diisopropyl peroxy dicarbonate, 2,2'-azobis(2,4-dimethylvaleronitrile), 2-t-butylazo-2-cyano-4-methoxy-4-methylpentane, 2,2'-azo-bis-2-methylbutanenitrile, 2-t-butylazo-2-cyanobutane, 1-t-amylazol-1-cyanocyclohexane, 2,2'-azobis(2,4-dimethyl-4-methoxyvaleronitrile, 2,2'-azo-bis-1 methylbutyronitrile, 2-t-butylazo-2-cyano-4-methylpentane, 2-t-butylazo-2-isobutyronitrile, to butylperoxyisopropyl carbonate and the like; a mixture of initiators may also be used. The preferred initiators are 2,2'-azobis(2-methylbutyronitrile), 2,2'-azobis(isobutyronitrile), 2,2'-azobis(2,4-dimethylvaleronitrile), 2-t-butylazo-2-cyano-4-methoxy-4-methyl pentane, 2-t-butylazo-2-cyano-4-methylpentane, 2-t-butylazo-2-cyano-butane and lauroyl peroxide, Generally, from about 0.1 percent to about 10 percent, preferably from about 1 percent to about 4 percent, by weight of initiator based on the weight of the monomer will be employed in the process of the invention.

Representative ethylenically unsaturated monomers which may be employed in the preparation of graft polymers used in the present invention include butadiene, isoprene, 1,4-pentadiene, 1,6-hexadiene, 1,7-octadiene, styrene, $\alpha$-methylstyrene, 2-methylstyrene, 3-methylstyrene, and 4-methylstyrene, 2,4-dimethylstyrene, ethylstyrene, isopropylstyrene, butylstyrene, and the like; substituted styrenes such as cyanostyrene, nitrostyrene, N,N-dimethylaminostyrene, acetoxystyrene, methyl 4-vinylbenzoate, phenoxystyrene, p-vinylphenyl oxide, and the like; the acrylic and substituted acrylic monomers such as acrylonitrile, acrylic acid, methacrylic acid, methyl acrylate, 2-hydroxyethyl acrylate, methyl methacrylate, cyclohexyl methacrylate, benzyl methacrylate, isopropyl methacrylate, octyl methacrylate, methacrylonitrile, ethyl $\alpha$-ethoxyacrylate, methyl $\alpha$-acetaminoacrylate, butyl acrylate, 2-ethylhexyl acrylate, phenyl acrylate, phenyl methacrylate, N,N-dimethylacrylamide, N,N-dibenzylacrylamide, N-butylacrylamide, methacrylyl formamide, and the like; the vinyl esters, vinyl ethers, vinyl ketones, etc., such as vinyl acetate, vinyl butyrate, isopropenyl acetate, vinyl formate, vinyl acrylate, vinyl methacrylate, vinyl methoxyacetate, vinyl benzoate, vinyltoluene, vinylnaphthalene, vinyl methyl ether, vinyl ethyl ether, vinyl propyl ethers, vinyl butyl ethers, vinyl 2-ethylhexyl ether, vinyl phenyl ether, vinyl 2-methoxyethyl ether, methoxybutadiene, vinyl 2-butoxyethyl ether, 3,4-dihydro-1,2-pyran, 2-butoxy-2'-vinyloxydiethyl ether, vinyl methyl ketone, vinyl ethyl ketone, vinyl phosphonates such as vinyl phenyl ketone, vinyl ethyl sulfone, N-methyl-N-vinyl acetamide, N-vinyl-pyrrolidone, vinyl imidazole, divinyl sulfoxide, divinyl sulfone, sodium vinylsulfonate, methyl vinylsulfonate, N-vinyl pyrrole and the like; dimethyl fumarate, dimethyl maleate, maleic acid, crotonic acid, fumaric acid, itaconic acid, monomethyl itaconate, t-butylaminoethyl methacrylate, dimethylaminoethyl methacrylate, glycidyl acrylate, allyl alcohol, glycol monoesters of itaconic acid, vinyl pyridine, and the like. Any of the known polymerizable monomers can be used and compounds listed above are illustrative and are not restrictive of the monomers suitable for use in this invention. Preferably, the monomer is selected from the group consisting of acrylonitrile, styrene, and mixtures thereof, and most preferably comprises a mixture of styrene and acrylonitrile.

The amount of polymerized ethylenically unsaturated monomer typically present in the graft polyol, alternatively known as the level of solids, ranges from 5 weight percent to about 50 weight percent, preferably from 10 weight percent to about 40 weight percent, based on the weight of the graft polyol, and most preferably from 20 to 40.

A particularly preferred isocyanate reactive component (b) will comprise a mixture of one or more of the foregoing polyoxyalkylene polyether polyols. In particular, it has been found that a preferred isocyanate reactive component (b) comprises (b 1 ) a propoxylated and ethoxylated diol initiated polyol having an OH number of from 10 to 40, (b2) a graft polyol having from 5 to 50 percent by weight of a polymerized ethylenically unsaturated monomer selected from the groups consisting of styrene, acrylonitrile, and mixtures thereof, in a carder polyol having a hydroxyl number of from 20 to 50, and (b3) a propoxylated and ethoxylated triol initiated polyol having an OH number of from 15 to 45.

More preferably, it has been found that polyol (b1) is a propoxylated and ethoxylated diol initiated polyol having a number average molecular weight of from 2000 to 7000, and more preferably from 2500 to 5000, and most preferably from 3500 to 4500. The polyol (b1) will preferably have a hydroxyl number of between 15 and 35, and most preferably from between 20 to 30. The percentage of residual alkylene oxide units attributable to propylene oxide should be between 65 to 95 percent, and more preferably from 75 to 85 percent, with the remaining residual alkylene oxide units being attributable to ethylene oxide. While suitable well-known diols such as propylene glycol, dipropylene glycol, 1,2-butanediol, 1,5-pentanediol, and the like are illustrative of suitable initiator molecules for polyol (b1), it has been found that the most preferred initiator is propylene glycol.

Graft polyol (b2) will most preferably have from between 10 to 55 percent by weight polymerized monomer, and more preferably from between 15 to 35 percent. While the foregoing discussion provides representative ethylenically unsaturated monomers which may be employed in the present invention, the most preferred monomer will be selected from the group consisting of acrylonitrile, styrene, and mixtures thereof, and most preferably will comprise a mixture of acrylonitrile and styrene. Polyol (b2) will generally have a number average molecular weight of from 3000 to 9000, preferably from 4000 to 7000, and most preferably from 4500 to 6500. The hydroxyl number for polyol (b2) will generally be from 10 to 40, preferably from 15 to 35, and most preferably from 20 to 30.

The carrier polyol for graft polyol (b2) will generally have a hydroxyl number of from 20 to 50, preferably from 25 to 45, and most preferably from 30 to 40. The molecular weight of the carrier polyol will generally be from between 2000 to 7000, preferably from 3000 to 6000, and most preferably from 3000 to 5000. While the carrier polyol may result from the reaction of one or more alkylene oxides with the polyhydric initiator molecules described above, it has been found that a preferred carrier polyol is one having a triol initiator and most preferably a triol such as glycerine or trimethylolpropane. In addition, it has been found that a mixture of propylene oxide and ethylene oxide is particularly advantageous, especially one wherein the resulting carder polyol has between 65 to 95 percent of residual alkylene oxide units attributable to propylene oxide and most preferably from 75 to 85 percent, with the remaining residual alkylene oxide units attributable to ethylene oxide.

With respect to polyol (b3), it has been found that a most preferred polyol is one having a hydroxyl number of from 15 to 45, preferably from 20 to 40, and most preferably from 25 to 35. The molecular weight of the triol initiated (b3) polyol will preferably be from between 2000 to 8000, and most preferably from between 3500 to 6500. While a variety of triol initiators may be utilized, it is most preferred that the triol be a material such as glycerine or trimethylolpropane, with glycerine being most preferred. Similarly, it has been found that it is most preferred that at least from 60 to 95 percent of the residual alkylene oxide groups be attributable to propylene oxide, more preferably 70 to 85 percent, with the remainder being residual ethylene oxide groups.

The polyurethane composition of the invention further comprises a blowing agent (c). While it is possible that blowing agent (c) may comprise other blowing agents in addition to water, it is most preferred that water be the sole or exclusive blowing agent. If other blowing agents in addition to water are utilized, they should generally be low boiling point liquids, generally organic compounds capable of vaporization under the influence of the reaction exotherm. Typical blowing agents will generally have a boiling point below 100° C. and include halogenated hydrocarbons such as, for example, methylene chloride, trichlorofluoromethane, and the like. Hydrocarbons such as pentane and formic acid are also suitable. When present, such physical blowing agents are to be used in an amount of from 0.1 to 16, preferably from 1 to 10, and more preferably from 2 to 6 weight percent by the weight of the total active hydrogen containing composition.

However, it is strongly preferred that water be the sole blowing agent. Those skilled in the art will appreciate that when water is referred to as the blowing agent, the actual agent of expansion is the carbon dioxide created in situ by the reaction of the water and the isocyanate groups.

Water as the sole blowing agent should generally be present in an amount of 0.02 to 1.00 based on pbw resin side (I). More preferably, the water will be present in an amount of from 0.30 to 0.50, and most preferably from 0.35 to 0.45.

The polyurethane composition of the invention will also contain a polyether (d). It has been found that the polyether (d) should be selected from the group consisting of polytetrahydrofuran and polyethylene glycol (PEG) having number average molecular weights of from 600 to 2000. If polytetrahydrofuran is used, it will preferably be Poly THF®[1] polytetrahydrofuran, commercially available from BASF Corporation of Wyandotte, Mich., Without wishing to be bound to a particular theory, it is believed that the incorporation of the polyether (d) of the foregoing type produces polymer units of a particular length, which in addition to the units resulting from isocyanate reactive component (b) and the particular units obtained with chain extender (e), combine to produce an integral skin polyurethane foam exhibiting superior physical properties. The polymer units resulting from the polyether (d) are believed to have a length in between those resulting from components (b) and (e).

[1] Poly THF® is a registered trademark of BASF Corporation.

Somewhat surprisingly, it has been found that, contrary to prior art teachings, the polyether (d) may be present in fairly minor amounts. By this it is meant that the polyether (d) will generally be present in an amount of less than 10 percent by weight, based on the total combined weight of the resin side (I), i.e., components (b), (c), (d), and (e). In particular, and most preferably, it has been found that the polyether (d) is present in an amount of less than 5 percent by weight, based on the total combined weight of (b), (c), (d), and (e). In particular, it is most preferred that polyether (d) be present in an amount of less than 3 percent by weight, based on the total combined weight of (b), (c), (d), and (e). It is believed that it is the unique combination of elements in the polyurethane composition of the invention which allows for the use of such low amounts of polyether (d) and which provides such cost and performance advantages.

When polyether (d) is a polytetrahydrofuran, it is particularly preferred that it be selected from the group having a number average molecular weight of between 800 to 2000, preferably from 1000 to 2000, and most preferably 1000. It has been found that polytetrahydrofuran results in particularly advantageous values in Taber abrasion resistance and tear strength.

When polyether (d) is a polyethylene glycol, it is preferred that it be selected from the group having a number average molecular weight of between 600 to 1000, and most preferably a molecular weight of approximately 600. PEG has been found to provide optimum values in tensile strength and percent elongation.

In addition to the foregoing elements, the polyurethane composition of the invention may further comprise one or more optional additives selected from the group consisting of catalyst, chain extenders, oxo alcohols and mixtures thereof.

Catalysts may be employed which greatly accelerate the reaction of the compounds containing hydroxyl groups with the modified or unmodified polyisocyanates. Examples of suitable compounds are cure catalysts which also function to shorten tack time, promote green strength, and prevent foam shrinkage. Suitable cure catalysts are organometallic catalysts, preferably organotin catalysts, although it is possible to employ metals such as lead, titanium, copper, mercury, cobalt, nickel, iron, vanadium, antimony, and manganese. Suitable organometallic catalysts, exemplified here by tin as the metal, are represented by the formula: $R_nSn[X-R^1-Y]_2$, wherein R is a $C_1-C_8$ alkyl or aryl group, $R^1$ is a $C_0-C_{18}$ methylene group optionally substituted or branched with a $C_1-C_4$ alkyl group, Y is hydrogen or an hydroxyl group, preferably hydrogen, X is methylene, an —S—, an —SR$^2$COO—, —SOOC—, an —O$_3$S—, or an —OOC— group wherein $R^2$ is a $C_1-C_4$ alkyl, n is 0 or 2, provided that $R^1$ is $C_0$ only when X is a methylene group. Specific examples are tin (II) acetate, tin (II) octanoate, tin (II) ethylhexanoate and tin (II) laurate; and dialkyl (1–8C) tin (IV) salts of organic carboxylic acids having 1–32 carbon atoms, preferably 1–20 carbon atoms, e.g., diethyltin diacetate, dibutyltin diacetate, dibutyltin diacetate, dibutyltin dilaurate, dibutyltin maleate, dihexyltin diacetate, and dioctyltin diacetate. Other suitable organotin catalysts are organotin alkoxides and mono or polyalkyl (1–8C) tin (IV) salts of inorganic compounds such as butyltin trichloride, dimethyl- and diethyl- and dibutyl- and dioctyl- and diphenyl-tin oxide, dibutyltin dibutoxide, di(2-ethylhexyl) tin oxide, dibutyltin dichloride, and dioctyltin dioxide. Preferred, however, are tin catalysts with tin-sulfur bonds which are resistant to hydrolysis, such as dialkyl (1–20C) tin dimercaptides, including dimethyl-, dibutyl-, and dioctyl- tin dimercaptides.

Tertiary amines also promote urethane linkage formation, and include triethylamine, 3-methoxypropyldimethylamine, triethylenediamine, tributylamine, dimethylbenzylamine, N-methyl-, N-ethyl- and N-cyclohexylmorpholine, N,N,N', N'-tetramethylethylenediamine, N,N,N',N'-tetramethylbutanediamine or -hexanediamine, N,N,N'-trimethyl isopropyl propylenediamine, pentamethyldiethylenetriamine, tetramethyldiaminoethyl ether, bis(dimethylaminopropyl)urea, dimethylpiperazine, 1-methyl-4-dimethylaminoethylpiperazine, 1,2-dimethylimidazole, 1-azabicylo[3.3.0]octane and preferably 1,4-diazabicylo[2.2.2]octane, and alkanolamine compounds, such as triethanolamine, triisopropanolamine, N-methyl- and N-ethyldiethanolamine and dimethylethanolamine.

Particularly suitable catalysts have been found to be dibutyltin dilaurate and tertiary amines, particularly triethylenediamine. Mixtures of such preferred catalysts are especially preferred.

Chain-extending agents which may optionally be employed in the preparation of the polyurethane foams include those compounds having at least two functional groups bearing active hydrogen atoms, and preferably having number average molecular weights less than 400, more preferably 60 to 300, such as water, hydrazine, primary and secondary diamines, amino alcohols, amino acids, hydroxy acids, glycols, or mixtures thereof. A preferred group of alcohol chain-extending agents includes water, ethylene glycol, 1,3-propanediol, 1,10-decanediol, o,-m,-p-dihydroxycyclohexane, diethylene glycol, 1,6-hexanediol, glycerine, trimethylol propane, 1,2,4-, 1,3,5-trihydroxycyclohexane, bis(2-hydroxyethyl) hydroquinone, 1,4-butanediol.

Examples of secondary aromatic diamines are N,N'-dialkyl-substituted aromatic diamines, which are unsubstituted or substituted on the aromatic radical by alkyl radicals, having 1 to 20, preferably 1 to 4, carbon atoms in the N-alkyl radical, e.g., N,N'-diethyl-, N,N'-di-sec-pentyl-, N,N'-di-sec-hexyl-, N,N'-di-sec-decyl-, and N,N'-dicyclohexyl-p- and m-phenylenediamine, N,N'-dimethyl-, N,N'-diethyl-, N,N'-diisopropyl-, N,N'-disec-butyl- and N,N'-dicyclohexyl-4,4'-diaminodiphenylmethane and N,N'-di-sec-butylbenzidine.

If aromatic diamines are used, it is best to use those which have at least one alkyl substituent in the orthoposition to the amino groups, are liquid at room temperature, and are miscible with the polyether polyols. Furthermore, alkyl-substituted meta-phenylenediamines of the formulae:

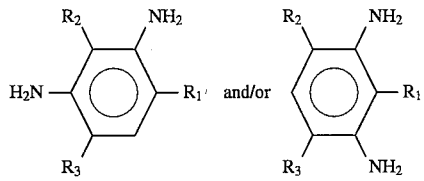

where $R_3$ and $R_2$ are identical or different and are methyl, ethyl, propyl, or isopropyl, and $R_1$ is linear or branched alkyl having 1 to 10 carbon atoms, preferably 4 to 6 carbon atoms, are useful.

Also useful are those alkyl radicals $R_1$ in which the branching point is on the $C_1$ carbon atom. Specific examples of radicals $R_1$ are methyl, ethyl, isopropyl, 1-methyloctyl, 2-ethyloctyl, 1-methylhexyl, 1,1-dimethylpentyl, 1,3,3-trimethylhexyl, 1-ethylpentyl, 2-ethylpentyl, and preferably cyclohexyl, 1-methyl-n-propyl, tert-butyl, 1-ethyl-n-propyl, 1-methyl-n-butyl and 1,1-dimethyl-n-propyl.

Specific examples of radicals $R_1$ are methyl, ethyl, isopropyl, 1-methyloctyl, 2-ethyloctyl, 1-methylhexyl, 1,1-dimethylpentyl, 1,3,3-trimethylhexyl, 1-ethylpentyl, 2-ethylpentyl and preferably cyclohexyl, 1-methyl-n-propyl, tert-butyl, 1-ethyl-n-propyl, 1-methyl-n-butyl, and 1,1-dimethyl-n-propyl.

Examples of suitable alkyl-substituted m-phenylenediamines are 2,4-dimethyl-6-cyclohexyl-, 2-cyclohexyl-4,6-diethyl-, 2-cyclohexyl-2,36-isopropyl-, 2,4-dimethyl-6-(1-ethyl-n-propyl)-, 2,4-dimethyl-6-(1,1-dimethyl-n-propyl)- and 2-(1-methyl-n-butyl)-4,6-dimethyl-1,3-phenylenediamine. Preference is given to 1-methyl-3,5-diethyl-2,4- and -2,6-phenylenediamines, 2,4-dimethyl-6-tert-butyl-, 2,4-dimethyl-6-isooctyl- and 2,4-dimethyl-6-cyclohexyl-1,3-phenylenediamine.

Examples of suitable 3,3'-di- and 3,3',5,5'-tetra-n- alkyl-substituted 4,4'-diaminodiphenylmethanes are 3,3'-di-, 3,3',5,5'-tetramethyl, 3,3'-di-, 3,3',5,5'-tetraethyl-, 3,3'-di- and 3,3',5,5'-tetra-n-propyl-4,4'-diaminodiphenylmethane.

Preference is given to diaminodiphenylmethanes of the formula:

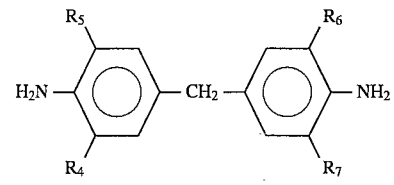

where $R_4$, $R_5$, $R_6$, and $R_7$ are identical or different and are methyl, ethyl, propyl, isopropyl, sec-butyl or tert-butyl, but where at least one of the radicals must be isopropyl or secu-butyl. The 4,4'-diaminodiphenylmethanes may also be used in a mixture with isomers of the formulae:

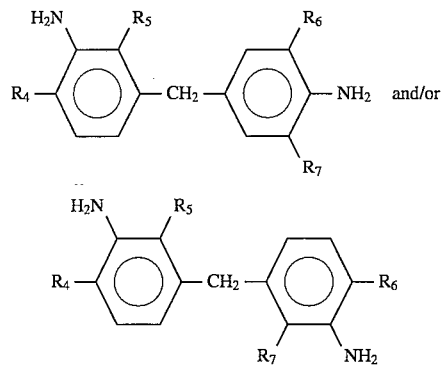

where $R_4$, $R_5$, $R_6$, and $R_7$ are as defined above.

Preference is given to 3,4-dimethyl-3', 5'-diisopropyl- and 3,3',5,5'-tetraisopropyl-4,4'-diaminodiphenylmethane. The diaminodiphenylmethanes can be employed individually or in the form of mixtures.

Of the foregoing, short chain diols are particularly preferred chain extending agents, especially those having from 7 to 4 carbon atoms. Particularly desirable chain extenders are 1,4-butanediol, ethylene glycol, diethylene glycol, tripropylene glycol, dipropylene glycol, and propylene glycol. 1,4-butanediol is especially preferred for use in shoe sole applications.

Additives (e) may include other alcohols typically described as oxoalcohols. Such alcohols are generally primary alcohols produced from monoolefins having from about 2 to about 20 carbons. With the exception of 2-ethylhexanol, oxoalcohols contain one more carbon than the starting olefin. They are generally supplied as a mixture of homologs and contain some branching. Examples of some commercially available products include LIAL 125 from Chemica Augusta Spa or NEODOL® 25 produced by Shell. Especially preferred is LIAL 125.

The additives (e) may further comprise other additives such as surfactants, fillers, UV stabilizers, pigments and mixtures thereof.

Examples of suitable surfactants are compounds which serve to support homogenization of the starting materials and may also regulate the cell structure of the plastics. Specific examples are salts of sulfonic acids, e.g., alkali metal salts or ammonium salts of fatty acids such as oleic or stearic acid, of dodecylbenzene- or dinaphthylmethanedisulfonic acid, and ricinoleic acid; foam stabilizers, such as siloxaneoxyalkylene copolymer and other organopolysiloxanes, oxyethylated alkyl-phenols, oxyethylated fatty alcohols, paraffin oils, castor oil esters, ricinoleic acid esters, Turkey red oil and groundnut oil, and cell regulators, such as paraffins, fatty alcohols, and dimethylpolysiloxanes. The surfactants are usually used in amounts of 0.01 to 5 parts by weight, based on 100 parts by weight of the polyol component.

The foams of the instant invention will be made by generally introducing the isocyanate component (a) and resin side (I) into a mold. Such molds will be well known to those skilled in the art. It will be appreciated that the mechanical parameters of the instant process are flexible and depend on the final application of the integral skin polyurethane foam. The polyurethane composition as disclosed herein is versatile enough that it may be made in a variety of densities and hardnesses. The system may be introduced into the mold in a variety of ways known to those skilled in the art. It may be shot into a preheated closed mold by a hard pressure injection technique. In this manner, the composition process is well enough to fill complex molds at low mold densities (from 18 pcf to 25 pcf). The composition may also be run using a conventional open mold technique when the reaction mixture or system is poured or injected at low pressure or atmospheric pressure into the preheated open mold. In such processes, the composition may be run at mold temperatures from about room temperature to about 120° F., with room temperature being preferred.

The integral skin polyeurethene foam articles resulting from the present invention are generally characterized by a surprisingly acceptable mix of physical performance properties, as well as a commercially acceptable look and feel. In particular, polyeurethene foam articles made according to the invention are specially suited for use as shoe soles.

In general, the integral skin polyeurethene molded articles of the invention are characterized by a tensile strength of greater than or equal to 450 psi. However, such articles preferably exhibit a tensile strength of greater than 475 psi, and most preferably greater than or equal to 500 psi. Tensile strength is measured according to ASTM D-3574.

In addition to tensile strength, taber abrasion (mg loss) is a particularly important property to the manufacturers of integral skin polyurethane foam shoe soles. In particular, such foams should have a taber abrasion (mg loss) of less than 200, preferably less than 190, and most preferably less than 180. Taber abrasion is measured per ASTM 1044.

Other important properties with respect to the foams of the invention are tensile elongation, split tear, graves tear, shore hardness, and ross flex. The testing methods for each property are indicated below.

| Test Methods | |
| --- | --- |
| Density ASTM D 3574 | Graves Tear ASTM D 3574 |
| Tensile Strength ASTM D 3547, Die A | Shore Hardness ASTM D 2240 |
| Split Tear ASTM D 3574 Elongation ASTM D 3574 | Ross Flex ASTM 1052 |

In general, foams according to the invention should have densities from 0.3 to 0.7 g/cc, preferably from 0.45 to 0.55 g/cc. Elongation should be greater than 300%, and most preferably greater than 400%. Split tear should be greater than 20 pi and most preferably greater than 30. Graves tear should be greater than 50 and most preferably greater than 65. Shore hardness should be from 40 to 60 and most preferably from 50 to 55. Ross flex (Kcycles at −20° F.) should be greater than 50, preferably greater than 80, and most preferably greater than 100.

Finally, it has been noted that the compositions of the invention are advantageous with respect to certain manufacturing problems typically encountered with integral skin polyurethane foams. That is, depending upon the size and dimension of the shoe sole mold, molded articles may exhibit shrinkage and inconsistency from article to article. As the following examples exhibit, the compositions of the invention more often than not produce molded shoe soles exhibiting acceptable levels of consistency and shrinkage.

The following examples are given by way of illustration only. All amounts are in parts by weight unless otherwise indicated.

Polyol A is a propylene glycol initiated polyoxypropylene polyoxyethylene block copolymer having a hydroxyl number of about 25 and a molecular weight of about 3850.

Polyol B is a 31 percent solids, 1:1, acrylonitrile:styrene graft copolymer dispersed, in a trimethylolpropane initiated polyoxypropylene-polyoxyethylene block copolymer having a molecular weight of about 4120. The graft polymer dispersion has a hydroxyl number of about 25.

Polyol C is a glycerine initiated polyoxypropylene-polyoxyethylene block copolymer having a hydroxyl number of about 27 and a molecular weight of about 5050.

Polyol D is a glycerine initiated polyoxypropylene-polyoxyethylene block copolymer having a hydroxyl number of about 35 and a molecular weight of about 4150.

Polyol E is a dipropylene glycol initiated polyoxypropylene-polyoxyethylene block copolymer having a hydroxyl number of about 29 and a molecular weight of about 3500.

Polyol F is a polypropylene glycol having a molecular weight of about 430 and a hydroxyl number of about 260.

Iso A is approximately 98% 4,4'-diphenylmethane diisocyanate and 2% 2,4'-diphenylmethane diisocyanate.

DABCO® S-25 is an amine catalyst blend of 25 percent triethylenediamine in 75 percent butanediol.

DABCO® T-12 is dibutyltin dilaurate commercially available from Air Products.

EXAMPLE 1

Preparation of Isocyanate Prepolymer (a)

| | |
| --- | --- |
| Isocyanate A | 66.5 percent |
| Benzoyl chloride | 0.015 percent |
| Polyol F | 2.402 percent |
| Dipropylene Glycol | 3.9999 percent |
| Polyol D | 13.462 percent |
| Polyol E | 13.622 percent |

Isocyanate A and the benzoyl chloride were charged to a preheated reactor. The reactor was started and the contents stirred throughout the operation. Contents of the reactor were heated to approximately 60° C., and the remaining ingredients added in sequence or as a blend maintaining temperature between 60° to 85° C. The contents were reacted for approximately two (2) hours at 80° to 90° C. The contents were cooled and sampled to determine the free NCO content. Target NCO was approximately 18.3 percent, and target viscosity approximately 1290 cps at 25° C.

EXAMPLE 2

Alternative Preparation of Isocyanate Prepolymer (a)
1. Preparation of Prepolymer 1

| Isocyanate A | 46.144 percent |
| Benzoyl chloride | 0.003 percent |
| Polyol D | 53.853 percent |

Molten isocyanate and benzoyl chloride were charged in a dry or nitrogen purged and preheated reactor. The agitator was turned on and batch temperature adjusted to approximately 60° C. Polyol D was added at a constant rate over a period of thirty (30) minutes. The contents of the reactor were reacted at approximately 80° C. for about one (1) hour. The reactor sample is taken and NCO determined and found to be approximately 14.1 percent. The reactor sample was cooled to 50° C. and transferred to storage containers.

2. Preparation of Prepolymer 2

| Isocyanate A | 45.464 percent |
| Benzoyl lendaury(?) chloride | 0.003 percent |
| Polyol E | 54.533 percent |

The method used was the same as used in the preparation of Prepolymer 1. The resulting NCO prepolymer 2 was 14.0 percent.

3. Preparation of Prepolymer 3

| Isocyanate A | 87.197 percent |
| Dipropylene Glycol | 7.999 percent |
| Polyol F | 4.804 percent |

Method

Isocyanate A was charged into a preheated reactor, and the contents were heated to approximately 105° C. The agitator was turned on and continued throughout the operation. A blend of dipropylene glycol and Polyol F were added to the reactor in a constant rate over a period of approximately one (1) hour with the temperature maintained at about 105° C. After completion of the addition, the contents were reacted for approximately 20 minutes at 105° C. The product was rapidly cooled to 40° C. and sampled and the NCO content determined. The NCO content was found to be 23.0 percent by weight.

4. Preparation of Isocyanate Prepolymer (a)

The isocyanate prepolymer composition (a) was prepared by mixing at 25° C. to 10° C., prepolymers 1, 2, and 3 in the following percent by weight: Prepolymer 1, 25.00 percent; Prepolymer 2, 25.00 percent; Prepolymer 3, 50.00 percent by weight. The NCO of the resulting prepolymer (a) was approximately 18.3 percent, and the viscosity was 1290 cps.

EXAMPLE 3

The isocyanate of Example 2 was added to the following resin (I) side composition at an isocyanate index of 100. The components were combined in a Puromat F-20 foam machine, commercially available from Linden Industries, and having a 2 component turn put of 3 to 10 lbs/min. The foam mixture was poured into a clean, dry 12"×6"×⅜" plaque mold coated with RCT A3315, a naptha based external mold release agent commercially available from Chemtrend. The mold was shut, and the foam allowed to cure. The finished plaque was demolded and tested. Table 1 shows the effect of varying the identity of polyether (d) in a comparison versus a commercial formulation using HFC-134a as a blowing agent.

| Component | Resin Side (I) pbw |
|---|---|
| Polyol A | 56.21 |
| Polyol B | 18.00 |
| Polyol C | 14.00 |
| 1,4-Butanediol | 6.0 |
| (Poly)tetrahydrofuran 1000 | 2.40 (or 2.4% PEG 600) |
| DABCO ® S-25 | 3.00 |
| Water | 0.36 |
| DABCO ® T-12 | 0.02 |

TABLE 1

| Property | 2.4% PTHF 1000 | 2.40% PEG 600 | WUC 40224 (commercial R-134a) |
|---|---|---|---|
| Density (pcf) | 30.36 | 30.02 | 31 |
| Tensile Strength (psi) | 614.6 | 528.4 | 550 |
| Elongation (%) | 337 | 310 | 370 |
| Split Tear (pi) | 28.6 | 30.1 | 40 |
| Graves Tear (pi) | 97.0 | 91.5 | 110 |
| Shore A instant 5 sec. | 50 | 49 | 55–60 |
|  | 47 | 47 |  |
| Taber Abrasion (mg loss) | 69.4 | 66.8 | 80 |
| Ross Flex on Bottoms Sole (Kcycles @ −20° C.) | 87 | >100 | >100 |

The above values indicate the performance of the invention in a laboratory setting. The values for taber abrasion are uncharacteristically low and are not believed to be representative of the performance of the instant invention.

EXAMPLE 4

Examples 4 and 5 indicate the effect of the idenity and molecular weight of polyether (d) on foam properties.
Hand-Mix The isocyanate of Example 2 was added to the resin side (I) formulations identified in Tables 2 and 4 at an isocyanate index of 100. The mixture was stirred from 7 to 10 seconds with a mix-blade at approximately 2,000 rpm and the resulting foam mixture poured into a 12"×6"×⅜" aluminum mold heated to 110° to 120° F. and coated with a commericially available silicone mold release agent (NIX STIX X-9022) from Dwight Products. The finished plaques were demolded and tested.

TABLE 2

FOAM FORMULATIONS

| Component | 1 pbw | 2 pbw | 3 pbw | 4 pbw | 5 pbw | 6 pbw | 7 pbw | 8 pbw | 9 pbw |
|---|---|---|---|---|---|---|---|---|---|
| Polyol A | 56.2 | 56.2 | 56.2 | 56.2 | 56.2 | 56.2 | 56.2 | 56.2 | 56.2 |
| Polyol B | 18 | 18 | 18 | 18 | 18 | 18 | 18 | 18 | 18 |
| Polyol C | 14 | 14 | 14 | 14 | 14 | 14 | 14 | 14 | 14 |
| 1,4-BDO | 6 | 6 | 6 | 6 | 6 | 6 | 6 | 6 | 6 |
| Water | 0.36 | 0.36 | 0.36 | 0.36 | 0.36 | 0.36 | 0.36 | 0.36 | 0.36 |
| Dabco S-25 | 3.0 | 3.0 | 3.0 | 3.0 | 3.0 | 3.0 | 3.0 | 3.0 | 3.0 |
| Dabco T-12 | 0.03 | 0.03 | 0.03 | 0.03 | 0.03 | 0.03 | 0.03 | 0.03 | 0.03 |
| PEG200 | 2.4 | | | | | | | | |
| PEG300 | | 2.4 | | | | | | | |
| PEG400 | | | 2.4 | | | | | | |
| PEG600 | | | | 2.4 | | | | | |
| PEG1000 | | | | | 2.4 | | | | |
| PTHF250 | | | | | | 2.4 | | | |
| PTHF650 | | | | | | | 2.4 | | |
| PTHF1000 | | | | | | | | 2.4 | |
| PTHF2000 | | | | | | | | | 2.4 |
| OH #/g Resin | 161.8 | 157.3 | 155.0 | 152.8 | 151.0 | 159.8 | 152.4 | 151.0 | 149.7 |
| 100 Res/( ) Iso: @100 Index | 66.2 | 64.4 | 63.5 | 62.6 | 61.8 | 65.4 | 62.4 | 61.8 | 61.3 |

TABLE 3

FOAM PHYSICAL PROPERTIES

| FORMULATION# | 1 | 2 | 3 | 4 | 5 | 6 | 7 | 6 | 9 |
|---|---|---|---|---|---|---|---|---|---|
| Component | PEG 200 | PEG 300 | PEG 400 | PEG 600 | PEG 1000 | PTHF 250 | PTHF 650 | PTHF 1000 | PTHF 2000 |
| % Shrink | −0.06 | −0.06 | −0.23 | −0.06 | 0.10 | −0.06 | −0.23 | 0.10 | 0.40 |
| Sectional Density | 28.8 | 30.1 | 26.3 | 29.3 | 28.8 | 26.4 | 29.7 | 30.0 | 27.7 |
| Tensile, psi | 221.0 | 250.2 | 234.4 | 295.1 | 221.0 | 253.4 | 252.6 | 268.0 | 279.0 |
| Elongation % | 143.3 | 190.0 | 173.3 | 236.7 | 143.3 | 183.3 | 173.3 | 176.7 | 206.7 |
| Split Tear, pi. | 28.25 | 25.30 | 28.40 | 27.28 | 28.25 | 22.25 | 29.95 | 32.50 | 26.30 |
| Graves Tear, pi. | 53.95 | 73.80 | 70.50 | 69.58 | 53.95 | 65.60 | 77.50 | 81.85 | 76.90 |
| Shore A Hardness | 43 | 39 | 36 | 37 | 43 | 38 | 40 | 44 | 36 |
| Instant 5 Second | 41 | 38 | 35 | 36 | 41 | 36 | 39 | 43 | 35 |
| Abrasion, mg. loss | 80.9 | 106.1 | 108.5 | 59.7 | 80.9 | 130.8 | 48.3 | 58.1 | 53.8 |
| Ross Flex (−20) | 500 | 500 | 500 | 500 | 500 | 500 | 500 | 500 | 500 |
| % Crack | 6.7 | 27.5 | 38.5 | 17.0 | 6.7 | 15.0 | 51.5 | 64.2 | 86.0 |
| Kcycles to Fail | | | | | | | | | |

EXAMPLE 5

TABLE 4

FOAM FORMULATIONS
Low Crosslinker Level

| Resin Side (I) Formulation | 1 | 2 | 3 | 4 | 5 | 6 | 7 | 8 | 9 |
|---|---|---|---|---|---|---|---|---|---|
| Component | pbw | pbw | pbw | pbw | pbw | pbw | pbw | pbw | pbw |
| P628 | 56.2 | 56.2 | 56.2 | 56.2 | 56.2 | 56.2 | 56.2 | 56.2 | 56.2 |
| P1198 | 18 | 18 | 18 | 18 | 18 | 18 | 18 | 18 | 18 |
| P1026 | 14 | 14 | 14 | 14 | 14 | 14 | 14 | 14 | 14 |
| 1,4-BDO | 6 | 6 | 6 | 6 | 6 | 6 | 6 | 6 | 6 |
| Water | 0.36 | 0.36 | 0.36 | 0.36 | 0.36 | 0.36 | 0.36 | 0.36 | 0.36 |
| Dabco DC-1 | 0.07 | 0.07 | 0.07 | 0.07 | 0.07 | 0.07 | 0.07 | 0.07 | 0.07 |
| Polycat SA-1 | 1.0 | 1.0 | 1.0 | 1.0 | 1.0 | 1.0 | 1.0 | 1.0 | 1.0 |
| Foamrez UL-1 | 0.06 | 0.06 | 0.06 | 0.06 | 0.06 | 0.06 | 0.06 | 0.06 | 0.06 |
| PEG200 | 2.4 | | | | | | | | |
| PEG300 | | 2.4 | | | | | | | |
| PEG400 | | | 2.4 | | | | | | |
| PEG600 | | | | 2.4 | | | | | |
| PEG1000 | | | | | 2.4 | | | | |
| PTHF250 | | | | | | 2.4 | | | |

TABLE 4-continued

FOAM FORMULATIONS
Low Crosslinker Level

| Resin Side (I) Formulation | 1 | 2 | 3 | 4 | 5 | 6 | 7 | 8 | 9 |
|---|---|---|---|---|---|---|---|---|---|
| PTHF650 | | | | | | | 2.4 | | |
| PTHF1000 | | | | | | | | 2.4 | |
| PTHF2000 | | | | | | | | | 2.4 |
| OH #/g Resin | 132.4 | 127.9 | 129.7 | 127.4 | 125.6 | 134.6 | 127.1 | 125.6 | 124.2 |
| 100 Res/( ) Iso: @ 100 Index | 55.3 | 53.4 | 54.1 | 53.2 | 52.4 | 56.2 | 53.0 | 52.4 | 51.8 |

TABLE 5

FOAM PHYSICAL PROPERTIES
Low Crosslinker Level

| FORMULATION# | 1 | 2 | 3 | 4 | 5 | 6 | 7 | 8 | 9 |
|---|---|---|---|---|---|---|---|---|---|
| Component | PEG 200 | PEG 300 | PEG 400 | PEG 600 | PEG 1000 | PTHF 250 | PTHF 650 | PTHF 1000 | PTHF 2000 |
| % Shrink | 0.75 | 1.41 | 0.59 | 1.25 | 0.75 | 1.08 | 1.25 | 1.08 | 0.92 |
| Sectional Density | 28.3 | 28.4 | 27.5 | 28.7 | 28.8 | 29.4 | 29.8 | 29.6 | 29.3 |
| Tensile, psi | 147.8 | 111.9 | 137.5 | 150.0 | 130.0 | 134.1 | 157.3 | 136.5 | 111.7 |
| Elongation, % | 250.0 | 206.6 | 236.6 | 333.3 | 315.0 | 220.0 | 305.0 | 220.0 | 210.0 |
| Split Tear, pi. | 22.52 | 35.90 | 30.56 | 30.69 | 27.31 | 33.19 | 32.40 | 33.22 | 35.09 |
| Graves Tear, Pi. | 35.46 | 57.17 | 51.75 | 53.80 | 40.49 | 47.45 | 45.54 | 60.29 | 53.28 |
| Shore A Hardness | 14 | 21 | 23 | 16 | 21 | 19 | 18 | 18 | 15 |
| Instant 5 Second | 14 | 20 | 21 | 16 | 20 | 19 | 18 | 18 | 15 |
| Abrasion | 74.4 | 91.7 | 97.1 | 73.1 | 39.9 | 180.8 | 114.4 | 87.8 | 119.7 |
| Ross Flex (−20) | 0 | 0 | 0 | 0 | 0 | 0 | 0 | 0 | 0 |
| % Crack Kcycles to fail | >100 | >100 | >100 | >100 | >100 | >100 | >100 | >100 | |

EXAMPLE 6

The composition of Example 3 was run in an industrial shoe sole maker's facility, except however, that the 1,4,BDO was increased 0.5% and water increased 0.40%. The components were combined in a low pressure foam machine at an isocyanate index of 100. The foam mixture was poured into one of three different shoe sole molds and one ¼" thick test plaque mold. Shoe soles produced from the various molds were evaluated for fit, feel, shrinkage and performance.

Process Parameters:

Mold Temperature=110°–120° F.

Demold Time=3 minutes

Mold Release=Chemtrend B5340

EVALUATION:

| Shoe Sole #1: | fit is fairly consistent from pair to pair (=2/32") units template 1/2 size up, 1/32" Shore A is 50–60 feel is slightly soft fill is acceptable |
|---|---|
| Shoe Sole #2: | fit is consistent from pair to pair units template 1/2 size up Shore A is 48–53 feel is very slightly soft fill is good |
| Shoe Sole #3: | fit is very inconsistent from pair to pair (2/32") units template to a size 13 to 14 MA Shore A is 54–60 feel is good fill is good |

Physical and Mechanical Properties:

| | 1/4" Test Parcel |
|---|---|
| Ross Flex @ −20° F. | >80K, cycles to failure |
| Ross Flex @ 0° F. | >84K, cycles to failure |
| Ross Flex @ RT | >100K, cycles to failure |
| Tensile Strength | 467 psi |
| Ultimate Elongation | 409% |
| Die C Tear Resistance | 673 pli |
| Taber Abrasion | 173 mg loss/K cycles |
| | Shoe Sole #1 |
| Ross Flex @ −20° F. | 36K, cycles to failure |
| Ross Flex @ 0° F. | 24, cycles to failure |
| Ross Flex @ RT | 46K, cycles to failure |
| | Shoe Sole #2 |
| Ross Flex @ −20° F. | 22K, cycles to failure |
| Ross Flex @ 0° F. | 84K, cycles to failure |
| Ross Flex @ RT | >100K, cycles to failure |
| | Shoe Sole #3 |
| Ross Flex @ −20° F. | >80K, cycles to failure |
| Ross Flex @ 0° F. | >84K, cycles to failure |
| Ross Flex @ RT | >100K, cycles to failure |

The mold for Shoe Sole #3 was exceptionally large, i.e., a man's 13–14 and is believed to be the reason for the variance in size consistency. The above numbers are believed to be somewhat lower than expected due to possible equipment variations.

It should be understood, of course, that while the invention herein shown and described can constitute a preferred embodiment of the invention, it is not intended to illustrate all possible forms thereof.

We claim:

1. An isocyanate composition comprising the reaction product of
   - (a1) a polyoxypropylated propylene glycol having an OH number from 200 to 300;
   - (a2) a diol selected from the group consisting of dipropylene glycol and tripropylene glycol;
   - (a3) a polyoxypropylated/ethoxylated glycerin having an OH number from 20 to 50;
   - (a4) a polyoxypropylated/ethoxylated glycol having an OH number from 15 to 45; and
   - (a5) diphenylmethane diisocyanate.

2. The isocyanate composition of claim 1 having a percent NCO of from 16 to 20.

3. The isocyanate composition of claim 2 having a percent NCO of from 17 to 19.

4. The isocyanate composition of claim 2 further comprising a blend of:
   - the reaction product of (a1) a polyoxypropylated propylene glycol having an OH number from 200 to 300, (a2) a diol selected from the group consisting of dipropylene glycol and tripropylene glycol, and (a5) diphenylmethane diisocyanate;
   - the reaction product of (a3) a polyoxypropylated/ethoxylated glycerin having an OH number from 20 to 50 and (a5) diphenylmethane diisocyanate; and
   - the reaction product of (a4) a polyoxypropylated/ethoxylated glycol having an OH number from 15 to 45, and (a5) diphenylmethane diisocyanate.

5. The isocyanate composition of claim 4 comprising:
   - from 20 to 70 percent by weight diphenylmethane diisocyanate;
   - from 1 to 30 percent by weight of an isocyanate terminated prepolymer which is the reaction product of (a1) a polyoxypropylated propylene glycol having an OH number from 200 to 300 with (a5) diphenylmethane diisocyanate;
   - from 5 to 40 percent by weight of an isocyanate terminated prepolymer which is the reaction product of (a2) a diol selected from the group consisting of dipropylene glycol and tripropylene glycol, and (a5) diphenylmethane diisocyanate;
   - from 1 to 30 percent by weight of an isocyanate terminated prepolymer which is the reaction product of (a4) a polyoxypropylated/ethoxylated glycol having an OH number from 15 to 45, and (a5) diphenylmethane diisocyanate; and
   - from 1 to 30 percent by weight of an isocyanate terminated prepolymer which is the reaction product of (a3) a polyoxypropylated/ethoxylated glycerin having an OH number from 20 to 50 and (a5) diphenylmethane diisocyanate.

* * * * *